United States Patent
Natori et al.

(10) Patent No.: US 10,342,415 B2
(45) Date of Patent: Jul. 9, 2019

(54) INSERTION APPARATUS

(71) Applicant: OLYMPUS CORPORATION, Tokyo (JP)

(72) Inventors: Yasuaki Natori, Akishima (JP); Fumiyuki Onoda, Tama (JP); Keijiro Omoto, Hachioji (JP); Takashi Yamashita, Hachioji (JP); Takashi Suzuki, Hino (JP); Yoshitaka Umemoto, Hachioji (JP); Takuro Onda, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/602,847

(22) Filed: May 23, 2017

(65) Prior Publication Data
US 2017/0251903 A1    Sep. 7, 2017

Related U.S. Application Data

(63) Continuation of application No. PCT/JP2016/060474, filed on Mar. 30, 2016.

(30) Foreign Application Priority Data

Apr. 8, 2015   (JP) ................... 2015-079411

(51) Int. Cl.
*A61B 1/00*    (2006.01)
*A61B 1/12*    (2006.01)
*G02B 23/24*   (2006.01)

(52) U.S. Cl.
CPC ........ *A61B 1/0016* (2013.01); *A61B 1/00006* (2013.01); *A61B 1/00073* (2013.01);
(Continued)

(58) Field of Classification Search
CPC .. A61B 1/00082; A61B 1/0058; A61B 1/0016
See application file for complete search history.

(56) References Cited

U.S. PATENT DOCUMENTS

2005/0272976 A1* 12/2005 Tanaka ............... A61B 1/00073
                                                600/114
2008/0086029 A1    4/2008 Uchiyama et al.
(Continued)

FOREIGN PATENT DOCUMENTS

JP       2008-93029 A     4/2008
JP       2011-172776 A    9/2011
(Continued)

OTHER PUBLICATIONS

International Search Report dated Jun. 14, 2016 received in PCT/JP2016/060474.
(Continued)

*Primary Examiner* — Alexandra L Newton
(74) *Attorney, Agent, or Firm* — Scully, Scott, Murphy & Presser, P.C.

(57) ABSTRACT

An insertion apparatus includes an insertion section, a motor that rotates a rotational housing, a drive control unit that supplies a driving current to the motor to control driving of the motor, a temperature detector provided in the rotational housing, that detects a temperature of the rotational housing, a temperature measurement unit that measures a temperature in a vicinity of the rotational housing based on a detection result obtained from the temperature detector, a heating element used for heating, and a heating control unit that controls the heating element to perform heating when a measurement result of the temperature measurement unit is lower than a predetermined temperature.

4 Claims, 8 Drawing Sheets

(52) U.S. Cl.
CPC ...... *A61B 1/00135* (2013.01); *A61B 1/00154* (2013.01); *A61B 1/128* (2013.01); *G02B 23/2476* (2013.01)

(56) References Cited

U.S. PATENT DOCUMENTS

| | | | |
|---|---|---|---|
| 2008/0262305 A1* | 10/2008 | Omoto | A61B 1/00154 600/118 |
| 2014/0221743 A1* | 8/2014 | Sugiyama | A61B 1/127 600/109 |
| 2014/0323878 A1 | 10/2014 | Toriumi et al. | |
| 2015/0313454 A1 | 11/2015 | Ide | |

FOREIGN PATENT DOCUMENTS

| | | | | |
|---|---|---|---|---|
| JP | 2013081656 A | * | 5/2013 | ............ A61B 1/127 |
| JP | 2014-64686 A | | 4/2014 | |
| WO | 2014/125850 A1 | | 8/2014 | |

OTHER PUBLICATIONS

English translation of International Preliminary Report on Patentability dated Oct. 19, 2017 together with the Written Opinion received in related International Application No. PCT/JP2016/060474.

Extended Supplementary European Search Report dated Jun. 29, 2018 in European Patent Application No. 16 77 6455.4.

\* cited by examiner

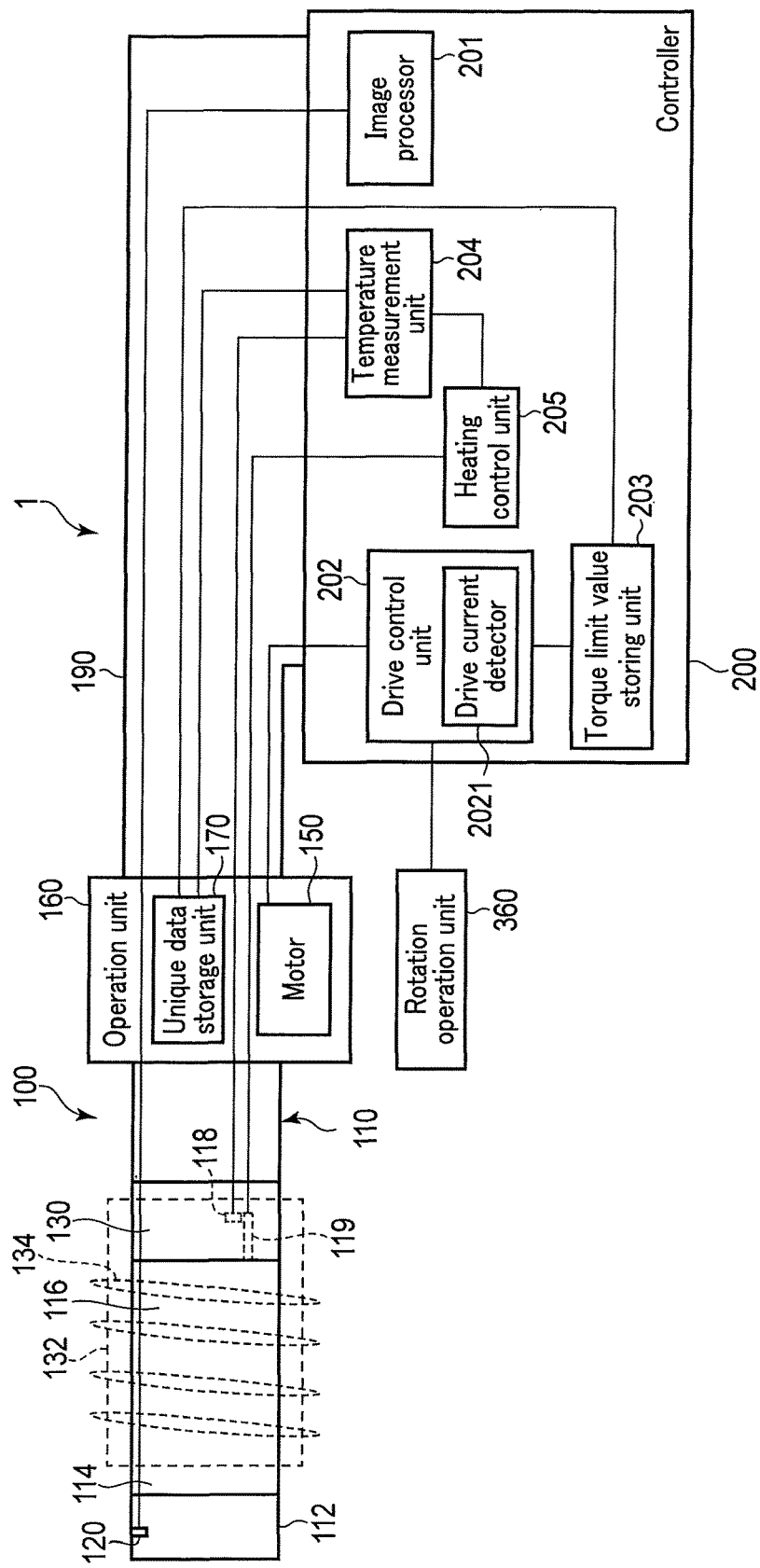
F I G. 1

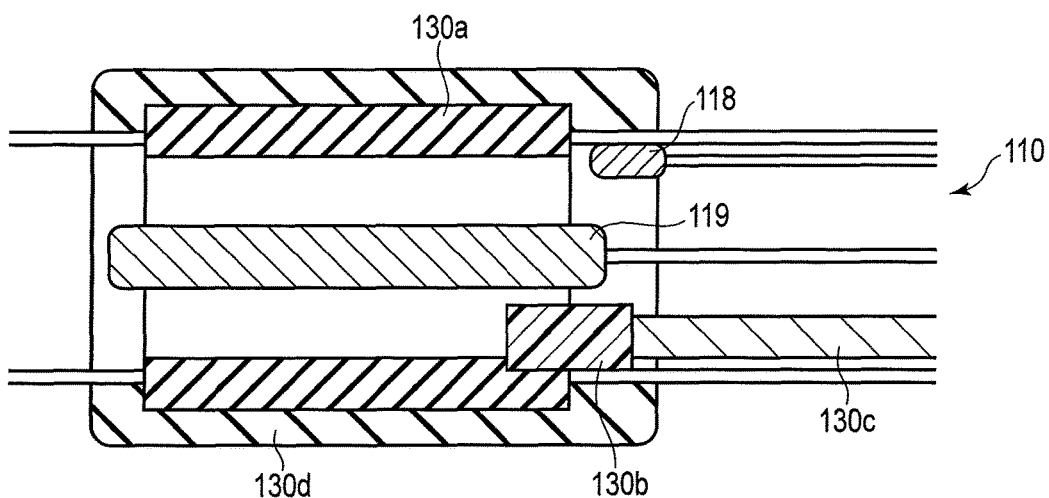
F I G. 2

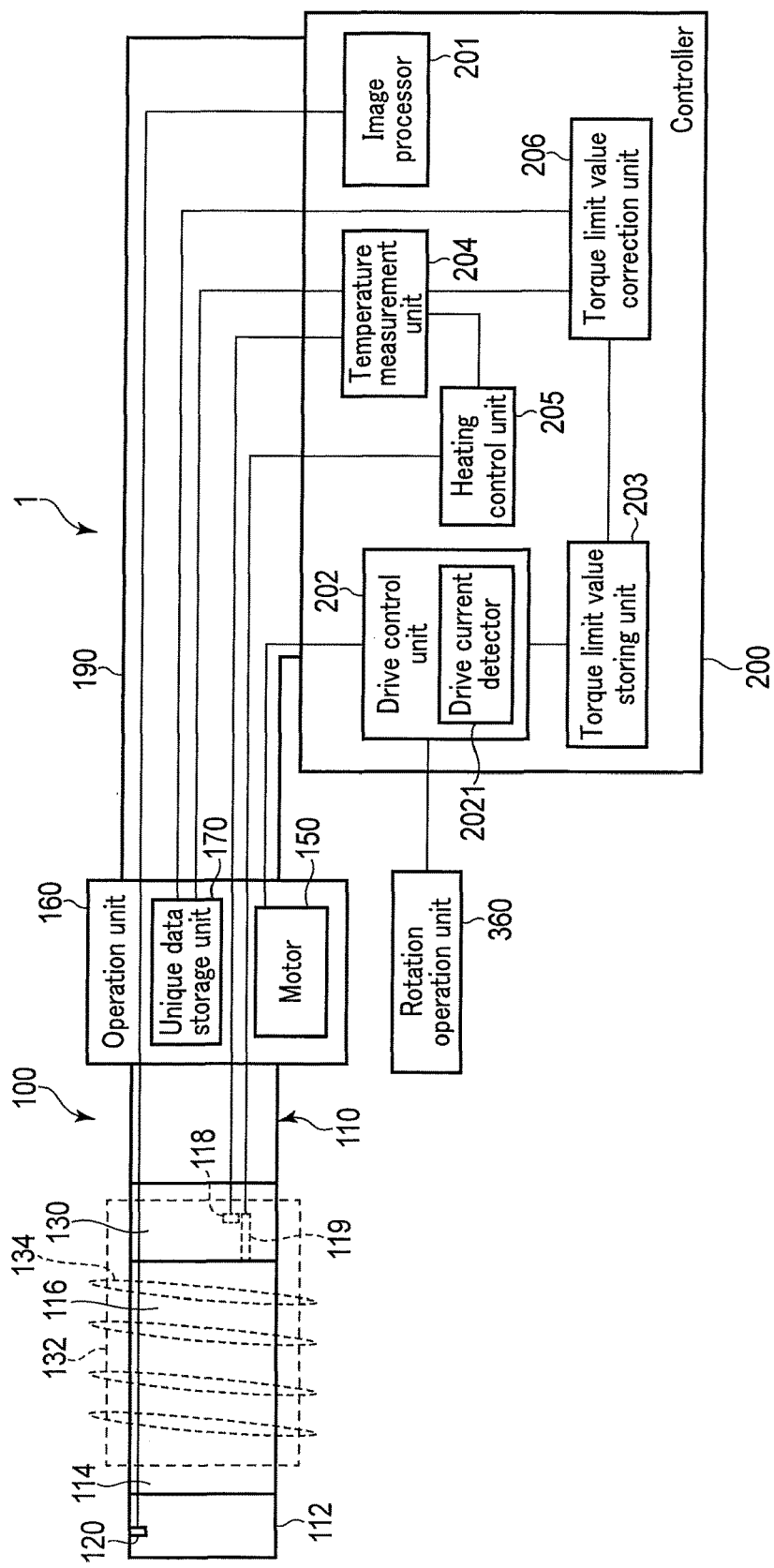
F I G. 5

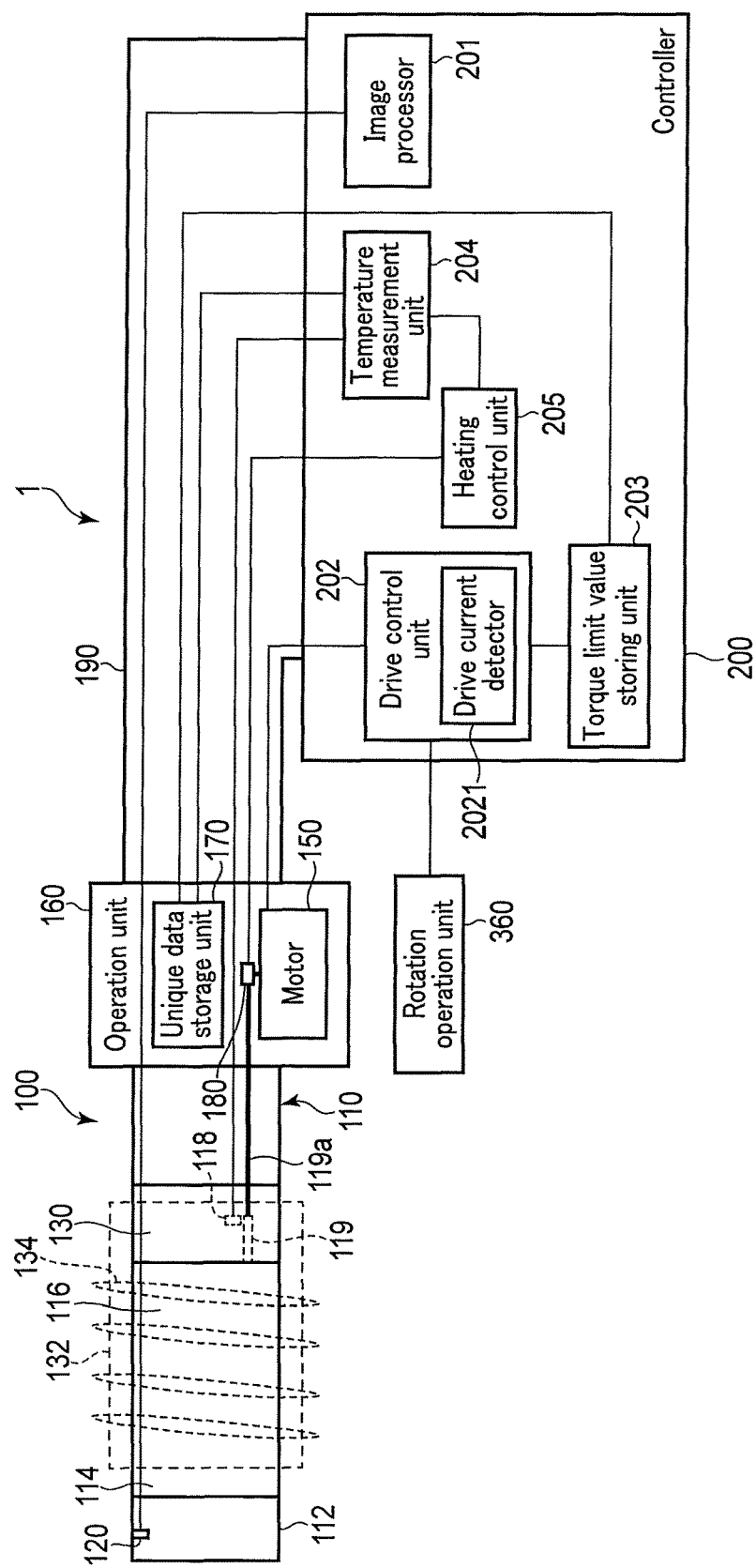
F I G. 8

INSERTION APPARATUS

CROSS-REFERENCE TO RELATED APPLICATIONS

This application is a Continuation Application of PCT Application No. PCT/JP2016/060474, filed Mar. 30, 2016 and based upon and claiming the benefit of priority from the prior Japanese Patent Application No. 2015-079411, filed Apr. 8, 2015, the entire contents of both of which are incorporated herein by reference.

BACKGROUND OF THE INVENTION

1. Field of the Invention

The present invention relates to a rotary self-propelled type insertion apparatus.

2. Description of the Related Art

Generally, an insertion apparatus such as an endoscope apparatus is inserted into a lumen. Among these types of insertion apparatuses, an insertion apparatus which is called a rotary self-propelled type has been known. The rotary self-propelled type endoscope apparatus is provided, for example, with a rotational housing which is called a spiral tube, etc. in which a spiral-shaped fin is formed on an outer peripheral surface of the insertion section. When the rotating housing is rotated, the fin formed to the rotational housing is brought into contact with an inner wall of a lumen, and generates friction. The insertion section self-propels in an insertion direction or in a removal direction by the friction. For example, Jpn. Pat. Appln. KOKAI Publication No. 2014-064686 provides suggestions regarding these types of self-propelled insertion apparatuses.

BRIEF SUMMARY OF THE INVENTION

An insertion apparatus according to an aspect of the invention comprises: an insertion section having an elongated shape; a rotational housing provided on an outer peripheral surface of the insertion section to be rotatable about a longitudinal axis; a motor that rotates the rotational housing; a drive control unit that supplies a driving current to the motor to control driving of the motor; a temperature detector provided in the rotational housing, that detects a temperature of the rotational housing; a temperature measurement unit that measures a temperature in a vicinity of the rotational housing based on a detection result obtained from the temperature detector; a heating element provided in the rotational housing and used for heating; and a heating control unit that controls the heating element to perform heating when a measurement result of the temperature measurement unit is lower than a predetermined temperature.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic view of a configuration of an endoscope system as an example of an insertion apparatus according to an embodiment of the present invention;

FIG. 2 is a cross-sectional view of an enlarged rotation section;

FIG. 5 is a diagram showing a configuration of an endoscope system of modification 1;

FIG. 8 is a diagram showing a configuration of an endoscope system of modification 2.

DETAILED DESCRIPTION OF THE INVENTION

Figure 3:
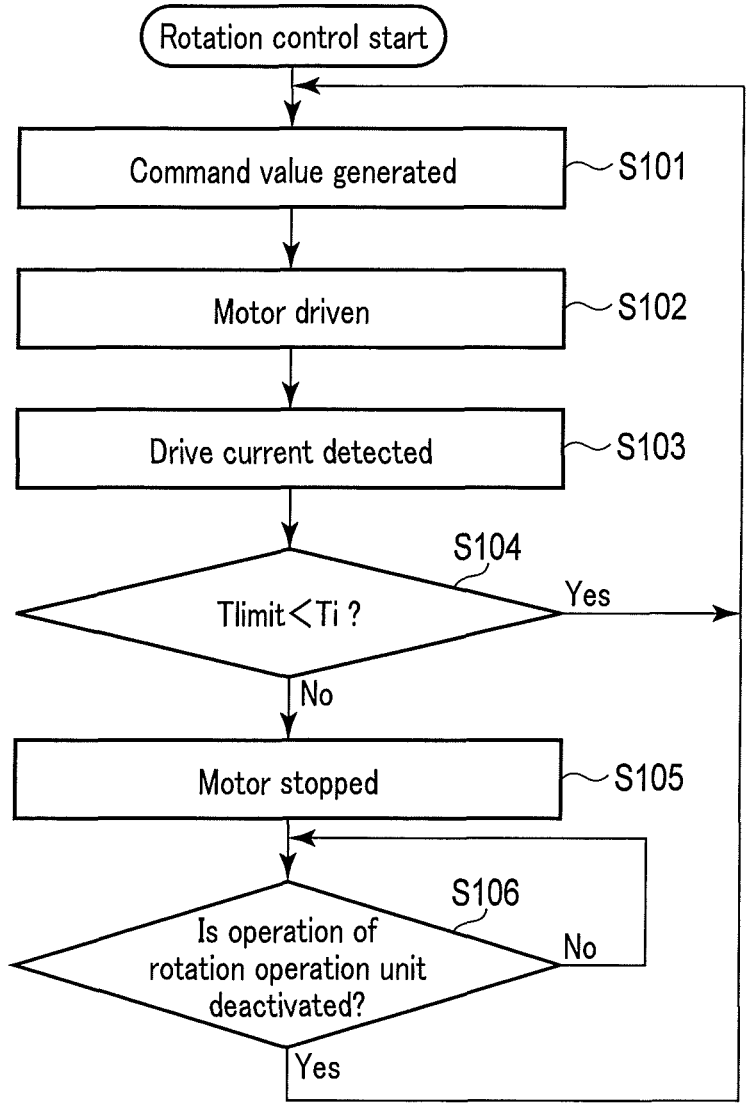
FIG. 3 is a flowchart of rotation control.

Hereinafter, an embodiment of the present invention will be described with reference to the drawings. FIG. 1 is a schematic view of a configuration of an endoscope system as an example of an insertion apparatus according to an embodiment of the present invention. As shown in FIG. 1, an endoscope system 1 includes an endoscope 100, a controller 200, and a rotation operation unit 360.

The endoscope 100 is a rotary self-propelled type endoscope, and includes an insertion section 110. The insertion section 110 is an elongated shape, and is configured to be inserted into a body. The endoscope 100 also includes an operation unit 160 attached to the insertion section 110, by which various operations for the endoscope 100 are performed. The operation unit 160 is held by a user. The operation unit 160 of the endoscope 100 and the controller 200 are connected by a universal cable 190. In the following explanation, the side of a distal end of the insertion section 110 is referred to as a distal end side. The side of the insertion section 110 at which the operation unit 160 is provided is referred to as a proximal end side. The direction from the distal end to the proximal end of the insertion section 110 is referred to as a longitudinal direction.

The insertion section 110 includes a distal end hard section 112, a bending section 114, and a coiled hose section 116. The distal end hard section 112 is an edge of the distal end of the insertion section 110, and is formed to not be bent. The distal end hard section 112 includes an imaging element 120. The imaging element 120 generates an image signal based on a subject image at the distal end side of the insertion section 110, for example. The image signal generated by the imaging element 120 is transmitted to an image processor 201 of the controller via an image signal line passing through the insertion section 110 and the universal cable 190. The bending section 114 is formed at the proximal end side of the distal end hard section 112, and is formed to be actively bent in accordance with an operation of an operation member (not shown in the drawings) provided to the operation unit 160. The coiled hose section 116 is formed at the proximal end side of the bending section 114, and is formed to be passively bent by external force.

The coiled hose section 116 is provided with a rotation section 130. The rotation section 130 is provided with a spiral tube 132 which is a rotational housing at the distal end. FIG. 2 is a cross-sectional view of the enlarged rotation section 130. As shown in FIG. 2, the rotation section 130 includes a housing 130a, a drive gear 130b, a drive shaft 130c, and a rotation transmission rubber 130d. The housing 130a is a cylindrical housing, and rotates in accordance with the rotation of a motor 150 built in the operation unit 160. The drive gear 130b is engaged with the housing 130a. The drive gear 130b transmits a driving power of the motor 150 transmitted from the drive shaft 130c to the housing 130a. The drive shaft 130c is connected to the motor 150, so as to rotate in accordance with the rotation of the motor 150, and to transmit the driving power of the motor 150 to the drive gear 130b. The rotation transmission rubber 130d has a cylindrical shape that covers an exterior of the housing 130a, and is a driving power transmission member that rotates in accordance with the rotation of the housing 130a and transmits the driving power of the motor 150 to the spiral tube 132.

The spiral tube 132 is formed of a soft material such as a rubber or a resin, for example, in a tubular shape. The spiral tube 132 is provided with a spiral fin 134 along the longitudinal axis of the spiral tube 132 on the outer peripheral surface. The spiral tube 132 may be configured to be removable from the rotation section 130.

A temperature sensor 118 that functions as a temperature detector is provided in the vicinity of the rotation section 130. The temperature sensor 118 is a sensor that detects the temperature inside of the rotation section 130, and preferably detects the temperature of the rotation transmission rubber 130d of the rotation section 130. An output signal of the temperature sensor 118 is transmitted to a temperature measurement unit 204 of the controller 200 through a sensor signal line passing through the insertion section 110 and the universal cable 190. For example, a contact type temperature sensor such as a thermocouple or a thermistor, or a non-contact type temperature sensor such as a radiation thermometer may be adopted as the temperature sensor 118. The contact type temperature sensor is disposed to be in contact with the rotation transmission rubber 130d, as shown in FIG. 2. The non-contact type temperature sensor is disposed in the vicinity of the rotation transmission rubber 130d. The temperature sensor 118 according to the present embodiment is not limited to a sensor having a particular structure, as long as it can detect the temperature of the vicinity of the rotation transmission rubber 130d. In an example shown in FIG. 2, the temperature sensor 118 is arranged to measure the temperature at a point of the rotation transmission rubber 130d. However, the temperature sensor 118 may be arranged to measure the temperature at multiple points of the rotation transmission rubber 130d. In this case, the average of the temperature measured at the multiple points, for example, is assumed to be the temperature of the rotation transmission rubber 130d.

A heater 119 which is used as a heating element is provided in the vicinity of the rotation section 130 of the insertion section 110. The heater 119 is a heating element that heats inside of the rotation section 130, preferably the rotation transmission rubber 130d of the rotation section 130. As shown in FIG. 2, for example, the heater 119 is provided inside of the rotation section 130. The heater 119 is connected to a heating control unit 205 of the controller 200 via a heater signal line passing through the insertion section 110 and the universal cable 190. The heater 119 heats the rotation section 130 in accordance with control by the heating control unit 205. A member that generates heat by allowing current to flow through a metallic resistant film such as nichrome, etc. is adopted as the heater 119. The heater 119 is not limited as long as the rotation section 130 can be heated from room temperature to body temperature, which is a temperature at which the rotation section 130 is used. For example, the heater 119 shown in FIG. 2 is a heating element that heats the rotation section 130 without contact, but may be an element that heats the rotation section 130 by being brought into contact with the rotation section 130.

The motor 150 is connected to a drive control unit 202 of the controller 200 via an actuator current signal line passing through the operation unit 160 and the universal cable 190.

The motor 150 operates by an operation using the rotation operation unit 360. The rotation power of the motor 150 is transmitted to the rotation section 130. As a result, the fin 134 provided in the spiral tube 132 rotates around the longitudinal axis. If the fin 134 rotates while being in contact with a wall part such as an inner paries of a lumen, friction is generated to allow the insertion section 110 to self-propel. For example, in a small intestine or a large intestine, if the fin 134 is in contact with folds in the inner paries of the small intestine or the large intestine, friction is applied to the insertion section 110. The insertion section 110 self-propels by the friction. The self-propelling of the insertion section 110 assists the insertion operation or the removal operation of the insertion section 110 by the user. The motor 150 includes a pulse generator. The pulse generator generates a pulse signal (rotational speed signal) in accordance with the rotational speed of the motor 150, and inputs the rotational speed signal to the controller 200 via a rotational speed signal line passing through the universal cable 190. The rotational speed of the motor 150 is controlled by the rotational speed signal.

The operation unit 160 is provided with a unique data storage unit 170. The unique data storage unit 170 stores data unique to the endoscope 100, such as a torque limit value, etc. The unique data storage unit 170 is formed, for example, of a nonvolatile memory. The torque limit value is a threshold of a driving current to activate a torque limit function. The torque limit value stored in the unique data storage unit 170 is a torque limit value at a predetermined set temperature (for example, body temperature (approximately 40° C.)), and the unique data storage unit 170 also stores the set temperature. The set temperature is preferably set depending on various conditions such as temperature properties of the rotation transmission rubber 130d or temperature properties of the motor 150.

The rotation operation unit 360 may be a footswitch, for example. The footswitch generates a command signal in accordance with a pressure amount applied to a pedal when a user stepped on the pedal.

The controller 200 controls each element of the endoscope system 1. The controller 200 includes the image processor 201, the drive control unit 202, a torque limit value storage unit 203, the temperature measurement unit 204 and the heating control unit 205.

The image processor 201 performs image processing to an image signal that is generated at the imaging element 120 and input to the image processor 201 through the insertion section 110 and the universal cable 190. The image processor 201 inputs the processed image signal to the display unit not shown in the drawings to display an endoscope image on the display unit.

The drive control unit 202 is configured, for example, by an ASIC, and acquires a command signal generated at the rotation operation unit 360 to convert it to a command value. In addition, the drive control unit 202 obtains a rotational speed signal of the motor 150. The drive control unit 202 then generates a driving power based on the command value and the rotational speed signal. The drive control unit 202 further supplies the driving power to the motor 150 to drive the motor 150. The drive control unit 202 includes a drive current detector 2021. The drive control unit 202 compares the driving current value with a torque limit value stored in the torque limit value storage unit 203, and stops the rotation of the motor 150 when the driving current reaches or exceeds the torque limit value. By the torque limit function, the generation of excessive torque by the motor 150 is suppressed. Accordingly, it is possible to reduce a possibility of applying unnecessary force to the inner paries of a lumen.

The torque limit value storage unit 203 reads a torque limit value from the unique data storage unit 170, and stores the read torque limit value. The torque limit value storage unit 203 is formed, for example, of a volatile memory.

The temperature measurement unit 204 measures the temperature of the rotation section 130 based on an output of the temperature sensor 118. For example, the temperature measurement unit 204 acquires a signal generated proportionally to the temperature detected by the temperature sensor 118, and converts the acquired signal into a temperature.

The heating control unit 205 includes a power supply for the heater 119. The heating control unit 205 compares the temperature measured at the temperature measurement unit 204 with the set temperature stored in the unique data storage unit 170, and allows the heater 119 to heat the rotation section 130 if the measured temperature is lower than the set temperature. Generally, the hardness of rubber changes depending on a change in temperature. If the hardness of the rotation section 130 changes, the operation of the spiral tube 132 is affected by the change. Accordingly, there is a possibility that the torque limit function, etc. is not normally activated. For example, there is a case where the torque limit function is not activated when the torque limit function should be activated, or the torque limit function is erroneously activated when the torque limit function is unnecessary. Thus, in the present embodiment, the temperature of the rotation transmission rubber 130d of the rotation section 130 is maintained to be the set temperature so that the rotation section 130 or the spiral tube 132 is operable under the same environment.

Figure 4:
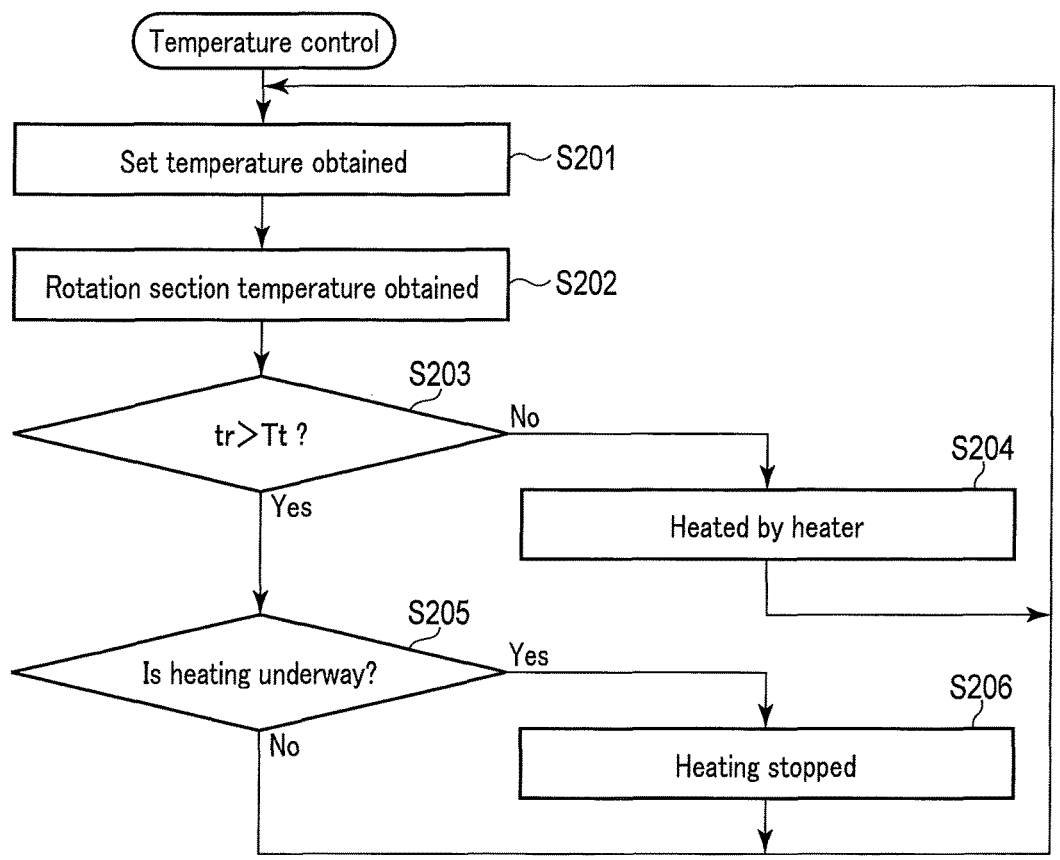
FIG. 4 is a flowchart of temperature control.

Next, the operation of the endoscope system 1 according to the present embodiment will be explained. FIG. 3 is a flowchart of rotation control of the motor 150 of the endoscope 100. FIG. 4 is a flowchart of temperature control of the rotation section 130. The controls of FIGS. 3 and 4 are performed asynchronously, for example. Of course, the controls of FIGS. 3 and 4 may be performed synchronously.

First, the rotation control will be explained with reference to FIG. 3. The operation shown in FIG. 3 is performed by the drive control unit 202. For example, the operation shown in FIG. 3 is initiated when the rotation operation unit 360 of the endoscope system 1 is operated. In step S101, the drive control unit 202 receives a command signal from the rotation operation unit 360, and generates, based on the command signal, a command value for the rotational speed in accordance with the pressing amount of the pedal of the rotation operation unit 360 by the user.

In step S102, the drive control unit 202 drives the motor 150 in accordance with the deviation between the command value and the current value of the rotational speed based on the rotational speed signal obtained from the pulse generator of the motor 150.

In step S103, the drive control unit 202 obtains a current driving current value Ti. In step S104, the drive control unit 202 compares the driving current value Ti and the torque limit value Tlimit stored in the torque limit value storage unit 203, and determines whether or not Tlimit is lower than Ti (Tlimit<Ti). In step S104, if it is determined that Tlimit<Ti is not satisfied, the processing returns to step S101. In step S104, if it is determined that Tlimit<Ti is satisfied, the processing proceeds to step S105.

In step S105, the drive control unit 202 enables the torque limit function to stop the power supplied to the motor 150 and to stop driving of the motor 150.

In step S106, the drive control unit 202 determines whether or not the operation of the rotation operation unit 360 is deactivated. In step S106, if it is determined that the operation of the rotation operation unit 360 is not deactivated, the processing stands by. In this case, the motor 150 remains stopped. In step S106, if it is determined that the operation of the rotation operation unit 360 is deactivated, the processing returns to step S101. In this case, the torque limit function is deactivated.

Next, the temperature control will be explained with reference to FIG. 4. The operation shown in FIG. 4 is performed by the heating control unit 205. For example, the operation shown in FIG. 4 is initiated when the endoscope system 1 is powered on. In step S201, the heating control unit 205 obtains a set temperature Tt stored in the unique data storage unit 170 of the endoscope 100 through the temperature measurement unit 204.

In step S202, the heating control unit 205 obtains a temperature tr of the rotation section 130 that is measured by the temperature measurement unit 204 based on an output of the temperature sensor 118.

In step S203, the heating control unit 205 compares the set temperature Tt with the rotation section temperature tr, and determines whether or not tr is higher than Tt (tr>Tt). In step S203, if it is determined that tr>Tt is not satisfied, the processing proceeds to step S204. In step S203, if it is determined that tr>Tt is satisfied, the processing proceeds to step S205.

In step S204, the heating control unit 205 controls the heater 119 to heat the rotation section 130. Subsequently, the processing returns to step S201.

In step S205, the heating control unit 205 determines whether or not the rotation section 130 is currently heated by the heater 119. In step S205, if it is determined that the rotation section 130 is not currently heated, the processing returns to step S201. In step S205, if it is determined that the rotation section 130 is currently heated, the processing proceeds to step S206.

In step S206, the heating control unit 205 controls the heater 119 to stop heating of the rotation section 130. Subsequently, the processing returns to step S201.

As explained above, according to the present embodiment, when the temperature of the rotation section 130 is below the set temperature, the rotation section 130 is heated to stably perform the torque limit function.

In the present embodiment, an example where the rotation section 130 is only heated is presented. It may be necessary not only to heat the rotation section 130 when the temperature becomes lower than the set temperature, but also to cool the rotation section 130 when the temperature becomes higher than the set temperature, in order to stably perform the torque limit function, as stated above. However, in the environment where the endoscope 100 is used, the endoscope 100, which is at room temperature of approximately 20° C., is inserted into a body (at approximately 36° C.). Accordingly, it is assumed that cooling is not necessary. Of course, the endoscope system 1 may be provided with a cooling mechanism that cools the rotation section 130 when the temperature becomes higher than the set temperature.

[Modification 1]

A modification of the present embodiment will be explained below. FIG. 5 is a diagram showing a configuration of an endoscope system of modification 1. The same structures as explained with reference to FIG. 1 are indicated with the same reference numerals, and the explanations thereof will be omitted.

Figure 6:
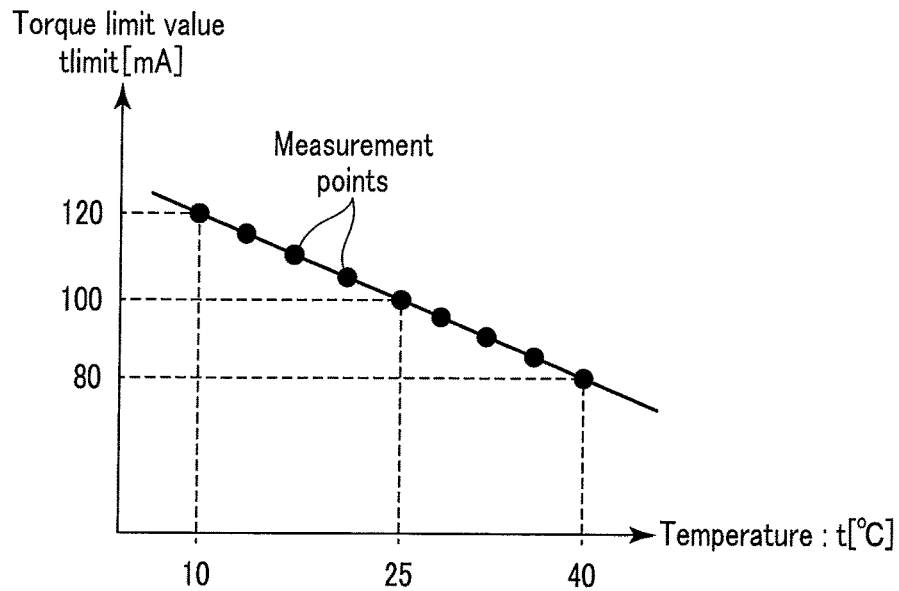
FIG. 6 is an example of a torque limit setting table.

A unique data storage unit 170 of modification 1 stores a torque limit setting table. The torque limit setting table is a table in which the temperature of a rotation section 130 and the torque limit value are associated. FIG. 6 is an example of a torque limit setting table. As shown in FIG. 6, the torque limit setting table is a table in which the torque limit values tlimit are associated with the temperatures in preset measurement points every 0.5° C. or 1° C. The torque limit value tlimit of the torque limit setting table is obtained by actual measurement, for example, and the values shown in FIG. 6 are merely an example. The torque limit value tlimit at a particular temperature between the measurement points shown in FIG. 6 is calculated by an interpolation operation using torque limit values tlimit at two closest measurement points that are lower or higher than the temperature.

In addition, a controller 200 of modification 1 is provided with a torque limit value correction unit 206. The torque limit value correction unit 206 obtains a torque limit value tlimit corresponding to the temperature measured at a temperature measurement unit 204 from the torque limit setting table, and overwrites the setting of a torque limit value storage unit 203.

Figure 7:
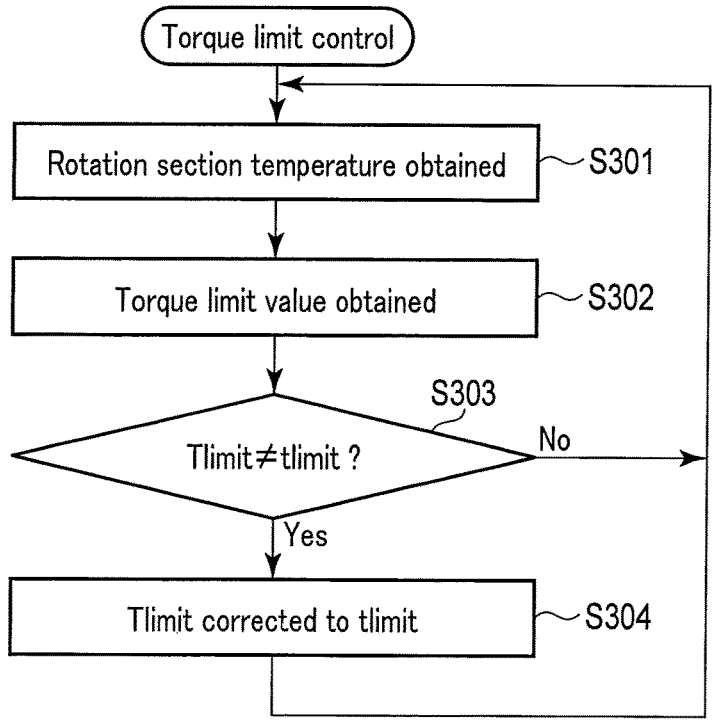
FIG. 7 is a flowchart of correction control for torque limit values.

FIG. 7 is a flowchart of correction control for torque limit values. The operation shown in FIG. 7 is performed by the torque limit value correction unit 206. The operation of FIG. 7 is performed asynchronously to the operations of FIGS. 3 and 4, for example. For example, the operation shown in FIG. 7 is initiated when the endoscope system 1 is powered on. In step S301, the torque limit value correction unit 206 obtains a temperature tr of the rotation section 130 that is measured by the temperature measurement unit 204 based on an output of the temperature sensor 118.

In step S302, the torque limit value correction unit 206 obtains a torque limit value tlimit in accordance with the temperature measurement result, from the torque limit setting table stored in the unique data storage unit 170 of the endoscope 100.

In step S303, the torque limit value correction unit 206 determines whether or not the torque limit value Tlimit stored in the torque limit value storage unit 203 is different from the torque limit value tlimit obtained in step S302. In step S303, if it is determined that the torque limit value Tlimit is not different from the torque limit value tlimit, the processing returns to step S301. In this case, the rotation control of FIG. 3 is performed with the torque limit value that has been stored in the torque limit value storage unit 203. In step S303, if it is determined that the torque limit value Tlimit is different from the torque limit value tlimit, the processing proceeds to step S304. In step S304, the torque limit value correction unit 206 performs correction to replace the torque limit value Tlimit with the torque limit value tlimit. Subsequently, the processing returns to step S301. In this case, the rotation control of FIG. 3 is performed with the replaced torque limit value.

As explained above, according to modification 1, it is possible to more stably enable the torque limit function, by correcting the torque limit value in accordance with the temperature, in addition to the temperature control of the rotation section 130.

[Modification 2]

Next, modification 2 will be explained. FIG. 8 is a diagram showing a configuration of an endoscope system of modification 2. The same structures as explained with reference to FIG. 1 are indicated with the same reference numerals, and the explanations thereof will be omitted.

In modification 2, a heater 119 is, for example, a metallic plate. The heater 119 is connected to a metal line 119a covered with a heat insulator. The metal line 119a is connected to a motor 150 through a switch 180. The switch 180 is connected to a heating control unit 205 through a signal line, and switches the state between the heater 119 and the motor 150 between a heat transfer state and a heat insulation state, in accordance with a control signal from the heating control unit 205.

In this configuration, the heating control unit 205 turns the switch 180 on when the temperature of a rotation section 130 is lower than the set temperature to change the state between the heater 119 and the motor 150 to be the heat transfer state. In this case, heat generated by driving the motor 150 is transmitted to the heater 119 through the metal line 119a. Then, the heater 119, which is a metallic plate for example, is heated, and accordingly, the rotation section 130 is heated.

According to modification 2, the heating control unit 205 may not have a power supply for the heater 119.

[Modification 3]

Figure 9:
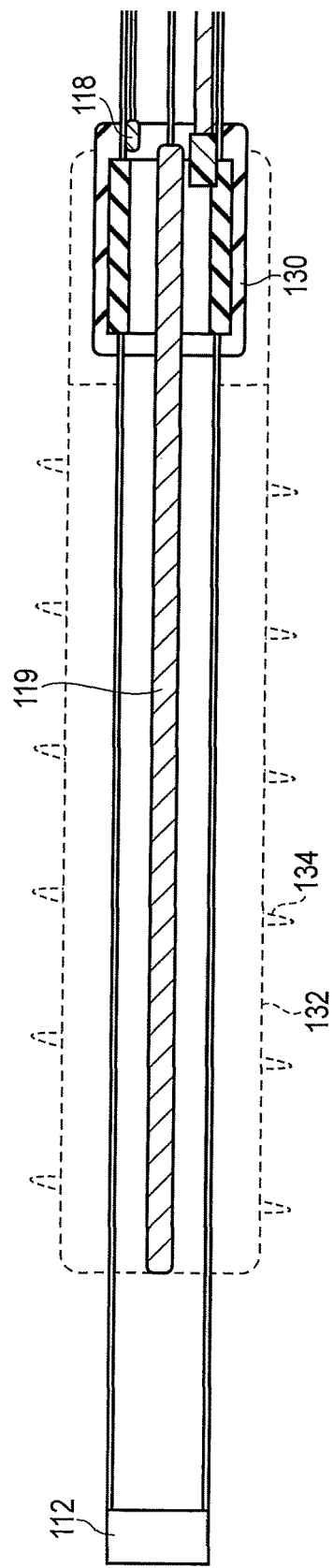
FIG. 9 is an enlarged diagram showing a rotation section and a vicinity of the rotation section of modification 3.

Next, modification 3 will be explained. FIG. 9 is an enlarged diagram showing a rotation section 130 and a vicinity of the rotation section 130 of modification 3. In modification 3, a heater 119 is provided to heat the entire spiral tube 132 including the rotation section 130. With this configuration, it is possible to control the entire temperature of the spiral tube 132 including the rotation section 130 to be a set temperature.

The present invention has been explained based on the embodiment; however, the present invention is not limited to the embodiment. The present invention may, of course, be modified in various ways without departing from the spirit and scope of the invention. In addition, the terms "first" or "next" are used for the explanation of the flowchart showing each operation; however, the sequence of the operation is not limited by these terms.

The operations described in the above embodiment may be stored in the form of programs executable by a CPU (which is a computer) or the like. The programs can be stored in storage mediums of external storage devices, such as a memory card, a magnetic disk, an optical disk or a semiconductor memory, and distributed. The CPU or the like reads the programs from a storage medium of an external storage device, and the operations can be executed and controlled based on the read programs.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion apparatus comprising:
   an insertion section having an elongated shape;

a rotational housing provided on an outer peripheral surface of the insertion section to be rotatable about a longitudinal axis;

a motor that rotates the rotational housing;

a heater arranged to provide heat to the rotational housing; and a controller comprising hardware, the controller being configured to:

supply a driving current to the motor to control driving of the motor;

measure a temperature in a vicinity of the rotational housing; and control the heater to perform heating when a measurement result the measured temperature is lower than a predetermined temperature;

wherein the heater comprises a metallic member connecting the motor to the rotational housing, the motor supplying heating energy to the rotational housing through the metallic member.

2. The insertion apparatus according to claim 1, further comprising a temperature sensor provided in the rotational housing that detects a temperature of the rotational housing.

3. The insertion apparatus according to claim 1, wherein the controller is further configured to:

detect the driving current;

store a torque limit value that is set in accordance with the driving current; and stop rotation of the motor when the driving current reaches or exceeds the stored torque limit value.

4. The insertion apparatus according to claim 1, wherein the heater is provided within the rotational housing.

* * * * *